United States Patent [19]

Nakanishi

[11] Patent Number: 4,533,324
[45] Date of Patent: Aug. 6, 1985

[54] AIR DRIVEN DENTAL HANDPIECE

[75] Inventor: Takasuke Nakanishi, Kanuma, Japan

[73] Assignee: Nakanishi Dental Mfg., Co., Ltd., Kanuma, Japan

[21] Appl. No.: 577,783

[22] Filed: Feb. 7, 1984

[30] Foreign Application Priority Data

Feb. 9, 1983 [JP] Japan ............................. 58-17728[U]

[51] Int. Cl.³ ............................................... A61C 1/05
[52] U.S. Cl. ..................................... 433/132; 433/126
[58] Field of Search ................................ 433/132, 126

[56] References Cited

U.S. PATENT DOCUMENTS

| | | | |
|---|---|---|---|
| 3,380,162 | 4/1968 | Heathe | 433/132 |
| 3,411,210 | 11/1968 | Staunt | 433/132 |
| 3,906,635 | 9/1975 | Lares et al. | 433/132 |
| 4,071,954 | 2/1978 | Eibofner | 433/132 |
| 4,219,330 | 8/1980 | Jaremus | 433/132 |

Primary Examiner—John J. Wilson
Attorney, Agent, or Firm—Wenderoth, Lind & Ponack

[57] ABSTRACT

An air driven dental handpiece has a turbine housing mounted on one end of a handle and an outwardly and upwardly tapered annular surface around the inner bottom surface of the housing. A turbine cartridge is removably mounted in the turbine housing and has an outwardly and upwardly tapered annular surface around the periphery of the bottom thereof abutting the tapered annular surface on the inner surface of the housing and an outwardly facing outwardly and downwardly tapered annular surface around the periphery of the top. An air turbine is rotatably mounted in ball bearings in the turbine cartridge, the turbine being resiliently mounted in the cartridge in the direction of the length of the turbine shaft. A head cap is threaded into the top of the turbine housing, and has a downwardly and outwardly tapered annular surface on the under side thereof abutting the downwardly and outwardly tapered annular surface on the upper end of the turbine cartridge for holding the turbine cartridge in a single fixed position in the turbine housing. One of said tapered annular surfaces in each pair of abutting tapered annular surfaces has an elastic sealing ring fitted in a slot therein and in sealing engagement with the other of the abutting pair of annular tapered surfaces.

1 Claim, 5 Drawing Figures

AIR DRIVEN DENTAL HANDPIECE

BACKGROUND OF THE INVENTION

This invention relates to improvements to a dental handpiece, and more particularly to an air driven dental handpiece having a turbine housing including a tapered annular inner portion around its inner bottom corner, a turbine cartridge inserted in the turbine housing, an air turbine, and a head cap.

Extremely high speeds have been attained utilizing pneumatically driven dental handpieces, and in the conventional air driven dental handpiece, a turbine cartridge inserted in a turbine housing with a slight clearance between the internal wall of the turbine housing and the turbine cartridge is fixedly held by a head cap, resulting in the vibration of the dental handpiece caused by the rotation of the air turbine, making a harsh noise and bringing about rapid wear of the air turbine.

The problem is further complicated by leakage of air under pressure, jamming and erratic operation.

SUMMARY AND OBJECTS OF THE INVENTION

A principal object of this invention is to provide an air driven dental handpiece which comprises a turbine housing including a tapered annular portion around its inner bottom corner, a turbine cartridge having tapered annular portions around its top and bottom peripheral corners, an air turbine, and a head cap whereby the turbine cartridge is fixedly held in the turbine housing by the head cap to drive the air turbine smoothly and with low noise.

Another object of this invention is to provide an air driven dental handpiece which includes elastic sealing rings interposed between the top and bottom tapered annular portions to eliminate lateral and longitudinal vibrations.

Another object of this invention is to provide an air driven dental handpiece whereby the tapered bottom and top outer portions of the turbine cartridge are brought into direct contact with the tapered annular inner portions of the turbine housing and of the head cap respectively without any clearance between them to prevent leakage of air under pressure.

Another object of this invention is to provide an air driven dental handpiece in which the lifetime of the air turbine can be considerably extended.

Another object of this invention is to provide an air driven dental handpiece which enables the dentist to accomplish his intended work accurately and easily.

Still another object of this invention is to provide an air driven dental handpiece which is comparatively simple and small, light in weight and at the same time desirably rigid, strong and durable.

BRIEF DESCRIPTION OF DRAWINGS

The above and further objects and novel features of the invention will more fully appear from the following detailed description when the same is read in connection with the accompanying drawings. It is to be expressly understood, however, that the drawings are for purpose of illustration only and are not intended as a definition of the limits of the invention.

DETAILED DESCRIPTION OF THE PREFERRED EMBODIMENT

Figure 1:
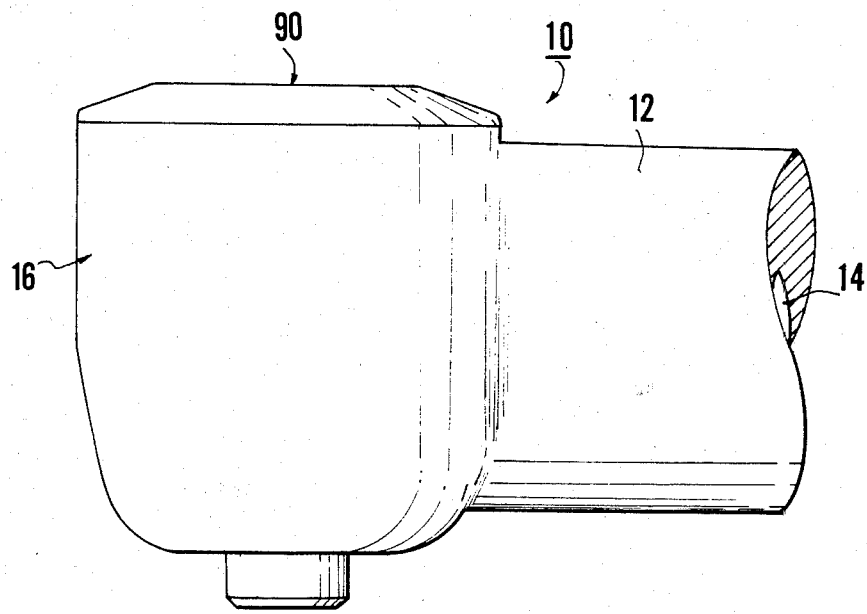
FIG. 1 is an enlarged elevation partly in section of a top portion of an air driven dental handpiece.
Figure 3:
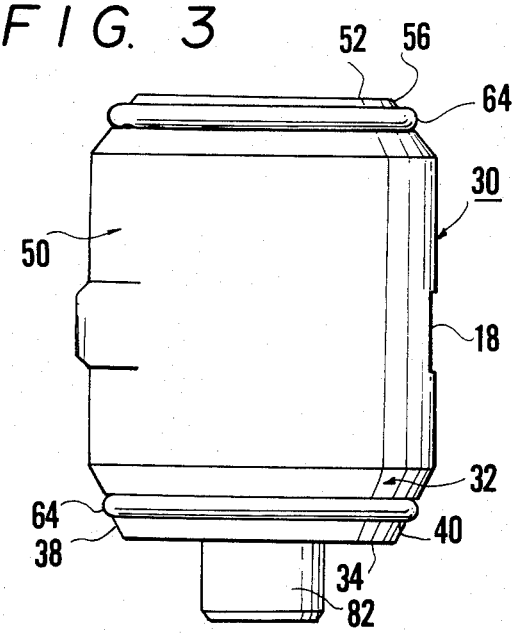
FIG. 3 is a front elevation of the turbine cartridge held in the turbine housing shown in FIGS. 1 and 2.
Figure 2:
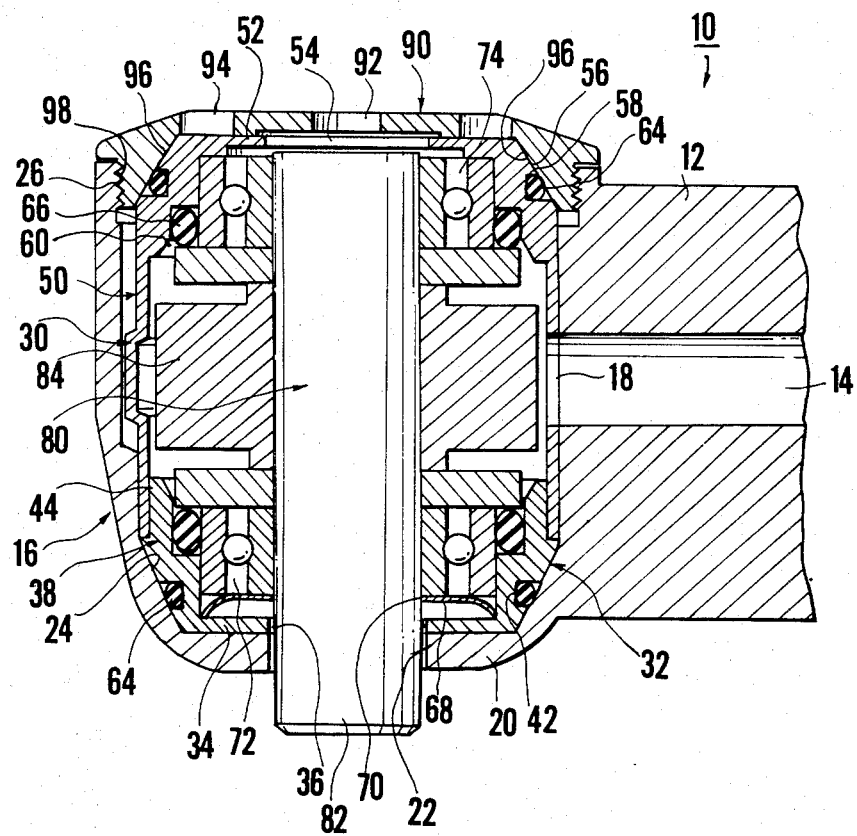
FIG. 2 is a vertical sectional view of the dental handpiece shown in FIG. 1.
Figure 4:
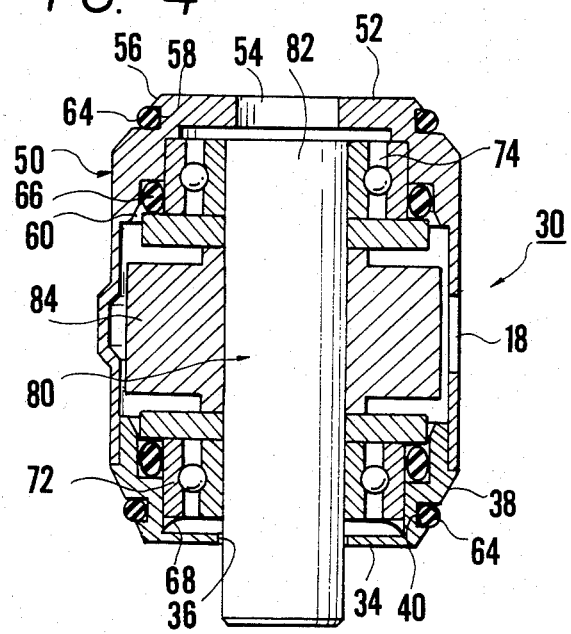
FIG. 4 is a vertical sectional view of the turbine cartridge shown in FIG. 3 with the turbine therein.
Figure 5:
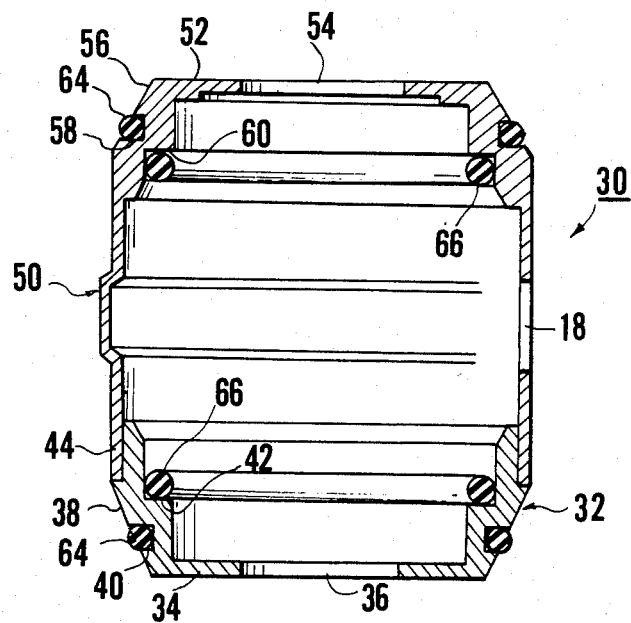
FIG. 5 is a greatly enlarged vertical sectional view of the turbine cartridge shown in FIG. 4 without the turbine therein.

Referring to the drawings, an air driven dental handpiece embodying the present invention is generally shown at 10 in FIGS. 1 and 2. The dental handpiece 10 comprises a handle portion 12 having an axial passage 14 for supplying air under pressure and a turbine housing 16 mounted perpendicularly at one end of the handle portion. The turbine housing 16 includes an opening 18 communicating with the axial passage 14 of the handle portion 12, and a bottom 20 having a central opening 22, an upwardly and outwardly tapered annular surface 24 around its inner bottom corner, and internal threads 26 around its top inner periphery. The openings 14 and 18 are used for supplying the air which drives the air turbine.

A turbine cartridge 30 includes a closed-end lower barrel 32 and a closed-end upper barrel 50 invertedly fitted onto the closed-end lower barrel 32. The lower closed-end barrel 32 has a bottom 34 having a central opening 36, an upwardly and outwardly tapered annular outer surface 38 complementary with the tapered annular surface 24 around the inner bottom corner of the turbine housing 16.

In addition, an inwardly recessed slot 40 is provided around the tapered annular outer surface 38 of the barrel 32, an indented portion 44 is formed around the top outer periphery, and a peripherally stepped portion 42 is provided around the inner middle periphery thereof. An elastic sealing ring 66 is fitted in the peripherally stepped annular portion 42, and an elastic sealing ring 64 is fitted in the inwardly recessed slot 40 so as to project only slightly out of the slot 40.

The closed-end upper barrel 50, which has an inner diameter to fit onto the indented outer peripheral portion 44, comprises a top plate 52 having a central opening 54, downwardly and upwardly tapered annular outer surface 56 around the top outer corner, and a peripherally stepped annular portion 60 around its inner periphery. An inwardly recessed slot 58 is provided around the tapered annular outer surface 56. An elastic sealing ring 66 is fitted in the stepped annular portion 60, and an elastic ring 64 is fitted in the inwardly recessed slot 58 so as to project only slightly out of the slot 58.

An inverted pan-shaped support 68 having a central opening 70 is disposed in the bottom of the closed-end lower barrel 32. A lower ball bearing 72 is disposed on the pan-shaped support 68.

The turbine cartridge 30 is inserted in the turbine housing 16 to bring the tapered annular outer surface 38 of the lower barrel 32 into direct contact with the tapered annular inner surface 24 of the turbine housing 16 with the elastic sealing ring 64 interposed between these tapered surfaces.

An air turbine 80, which comprises a rotor shaft 82 and a plurality of radially extending blades 84, is rotatably mounted in the lower ball bearing 72 and in an upper ball bearing 74 disposed in the upper portion of the upper barrel 50. A dental tool (not shown) is secured into the air turbine 80.

The turbine cartridge 30 comprises a single unit consisting of the upper and lower ball bearings 72 and 74, and the air turbine 80. The turbine cartridge 30 is integrally insertable and removable from the turbine housing 16. The rotor shaft 82 extends perpendicularly to the handle portion 12 of the dental handpiece 10.

A head cap 90 which has downwardly and outwardly tapered annular surface 96 and external threads 98 is provided with a central exhaust opening 92 and a pair of diametrically provided openings 94 for a wrench.

The head cap 90 is threadedly secured on threads 26 around an inner top periphery of the turbine housing 16 to bring the tapered annular inner surface 96 into direct contact with the surface 56 with the elastic sealing ring 64 interposed between the surfaces portions so that the turbine cartridge 30 is held fixed in the turbine housing 16.

As particularly seen in FIG. 2, the inner bottom corner 24 of the turbine housing 16 is formed into a tapered annular surface and the top peripheral inner portion is formed into a cylindrical hollow so that the turbine cartridge 30 can be inserted therein quite easily.

The tapered annular outer surface 38 of the turbine cartridge 30 is closely brought into contact with the tapered annular surface 24 of the turbine housing 16 with the elastic sealing ring 64 interposed between the tapered annular surfaces 24 and 38, and the top tapered annular outer surface 56 is closely brought into contact with the tapered annular inner surface 96 of the head cap 90 with the elastic sealing ring 64 interposed between the tapered annular surfaces 56 and 96. Accordingly, the turbine cartridge 30 is fixedly held in position in the turbine housing 16 to locate the air turbine 80 perpendicularly to the handle portion 12 and also to eliminate the lateral and longitudinal vibrations of the air turbine 80.

The insertion and removal of the air turbine 80 can be easily carried out by unscrewing and screwing the head cap 90.

From the foregoing, it is believed that the features and advantages of my invention will be readily apparent to those skilled in the art and it will be understood that changes in the form, proportion and minor details of construction may be resorted to without departing from the spirit or scope of the appended claims.

I claim:

1. An air driven dental handpiece comprising:

a handle portion having an axial passage for supplying air under pressure;

a turbine housing mounted on one end of said handle portion and having an axis extending perpendicular to the axis of the handle portion, said turbine having an opening therein communicating with said axial passage in said handle portion, having a bottom with a central opening therein, an outwardly and upwardly tapered annular surface around the inner bottom surface of said bottom, and internal threads around the inner peripheral surface of the top of said turbine housing;

a turbine cartridge removably mounted in said turbine housing, said turbine cartridge having a closed lower end and a closed upper end, said closed lower end having a central opening and an outwardly facing outwardly and upwardly tapered annular surface around the periphery thereof abutting said tapered annular surface on the inner surface of said bottom, said closed upper end having a central opening and an outwardly facing outwardly and downwardly tapered annular surface around the periphery thereof;

ball bearings in the lower and upper parts of said tubine cartridge;

an air turbine rotatably mounted in said turbine cartridge and having a rotor shaft mounted in said ball bearings and radially extending turbine blades mounted on said shaft, said rotor shaft extending perpendicularly to said handle portion and said shaft, blades and bearings being resiliently mounted in said cartridge in the direction of the length of said shaft;

a head cap having a central exhaust opening and external threads around the periphery thereof threaded into the internal threads around the peripheral surface at the top of said turbine housing, said cap having a downwardly and outwardly tapared annular surface on the under side thereof abutting said downwardly and outwardly tapered annular surface on the upper end of said turbine cartridge for holding said turbine cartridge in a single fixed position in said turbine housing;

at least one of said tapered annular surfaces in each pair of abutting tapered annular surfaces having an inwardly recessed slot therein; and elastic sealing rings fitted in said inwardly recessed slots and in sealing engagement with the other of the abutting pair of annular tapered surfaces.

* * * * *